(12) United States Patent
Junger et al.

(10) Patent No.: US 11,076,933 B2
(45) Date of Patent: Aug. 3, 2021

(54) AUTHENTICATION SYSTEMS AND METHODS FOR AN EXCIMER LASER SYSTEM

(71) Applicant: ELT SIGHT, INC., Los Angeles, CA (US)

(72) Inventors: Johannes Junger, Gilching (DE); Markus Enders, Munich (DE)

(73) Assignee: ELT SIGHT, INC., Los Angeles, CA (US)

( * ) Notice: Subject to any disclaimer, the term of this patent is extended or adjusted under 35 U.S.C. 154(b) by 0 days.

(21) Appl. No.: 16/389,346

(22) Filed: Apr. 19, 2019

(65) Prior Publication Data

US 2020/0330181 A1    Oct. 22, 2020

(51) Int. Cl.
*G06K 19/077* (2006.01)
*A61B 90/98* (2016.01)
*A61F 9/008* (2006.01)

(52) U.S. Cl.
CPC .......... *A61B 90/98* (2016.02); *A61F 9/00814* (2013.01); *G06K 19/077* (2013.01)

(58) Field of Classification Search
CPC .... A61B 90/98; A61F 9/00814; G06K 19/077
USPC ....................................................... 235/375
See application file for complete search history.

(56) References Cited

U.S. PATENT DOCUMENTS

| 4,607,622 | A | 8/1986 | Fritch et al. |
| 5,323,766 | A | 6/1994 | Uram |
| 5,738,677 | A | 4/1998 | Colvard et al. |
| 6,283,974 | B1 | 9/2001 | Alexander |
| 6,743,221 | B1 | 6/2004 | Hobart et al. |
| 2004/0082939 | A1 | 4/2004 | Berlin |
| 2005/0192480 | A1 | 9/2005 | Toriya et al. |
| 2006/0244652 | A1* | 11/2006 | Tethrake ............... A61B 90/00 342/44 |
| 2007/0122096 | A1 | 5/2007 | Temelkuran et al. |
| 2007/0147752 | A1 | 6/2007 | Weisberg et al. |
| 2007/0219601 | A1 | 9/2007 | Neuberger |
| 2007/0265602 | A1 | 11/2007 | Mordaunt et al. |
| 2008/0054073 | A1* | 3/2008 | Charles ............... G06Q 10/087 235/385 |
| 2008/0082078 | A1 | 4/2008 | Berlin |
| 2008/0097415 | A1 | 4/2008 | Zimare et al. |
| 2008/0108981 | A1 | 5/2008 | Telfair et al. |
| 2008/0108983 | A1 | 5/2008 | Nadolski |

(Continued)

FOREIGN PATENT DOCUMENTS

| DE | 19920615 A1 | 12/2000 |
| DE | 10023176 A1 | 11/2001 |

(Continued)

OTHER PUBLICATIONS

Crandall, Alan, "Combining Cataract and Glaucoma Surgery", Review of Ophthalmology, 1-4, Jun. 13, 2008.

(Continued)

*Primary Examiner* — Michael G Lee
*Assistant Examiner* — David Tardif
(74) *Attorney, Agent, or Firm* — Greenberg Traurig, LLP; Roman Fayerberg; David J. Dykeman

(57) ABSTRACT

The invention provides an excimer laser system including a means for authenticating laser probes to be used with the excimer laser system via radio-frequency identification techniques.

15 Claims, 5 Drawing Sheets

(56) References Cited

U.S. PATENT DOCUMENTS

| | | |
|---|---|---|
| 2009/0118715 A1 | 5/2009 | Mansour |
| 2009/0157064 A1 | 6/2009 | Hodel |
| 2010/0019125 A1 | 1/2010 | Stefani et al. |
| 2010/0324543 A1 | 12/2010 | Kurtz et al. |
| 2013/0041357 A1* | 2/2013 | Neuberger ............. A61N 5/062 606/15 |
| 2013/0085484 A1 | 4/2013 | van Valen et al. |
| 2014/0058367 A1 | 2/2014 | Dantus |
| 2014/0188096 A1 | 7/2014 | Chia et al. |
| 2014/0316388 A1 | 10/2014 | Hipsley |
| 2015/0148615 A1 | 5/2015 | Brennan et al. |
| 2015/0297408 A1 | 10/2015 | Dolzan et al. |
| 2015/0374549 A1* | 12/2015 | Scott ................... A61F 9/00836 606/5 |
| 2017/0100041 A1 | 4/2017 | Kasamatsu et al. |
| 2017/0202708 A1 | 7/2017 | Berlin |
| 2017/0304001 A1 | 10/2017 | Searle et al. |
| 2018/0000337 A1 | 1/2018 | Chen et al. |
| 2018/0042772 A1 | 2/2018 | Mansour |
| 2018/0263647 A1* | 9/2018 | Aljuri .................... A61B 8/085 |
| 2018/0353328 A1 | 12/2018 | Bacher et al. |
| 2018/0360310 A1 | 12/2018 | Berlin |
| 2019/0105200 A1 | 4/2019 | Hipsley |
| 2020/0330157 A1 | 10/2020 | Junger et al. |
| 2020/0330266 A1 | 10/2020 | Junger et al. |
| 2020/0330274 A1 | 10/2020 | Junger et al. |
| 2020/0330275 A1 | 10/2020 | Junger et al. |
| 2020/0330279 A1 | 10/2020 | Junger et al. |
| 2020/0330280 A1 | 10/2020 | Junger et al. |
| 2020/0330281 A1 | 10/2020 | Junger et al. |

FOREIGN PATENT DOCUMENTS

| | | |
|---|---|---|
| EP | 1835862 B1 | 6/2011 |
| WO | 2020215062 A1 | 10/2020 |
| WO | 2020215064 A1 | 10/2020 |
| WO | 2020215067 A1 | 10/2020 |
| WO | 2020215068 A1 | 10/2020 |
| WO | 2020215069 A1 | 10/2020 |
| WO | 2020215071 A1 | 10/2020 |
| WO | 2020215073 A1 | 10/2020 |

OTHER PUBLICATIONS

Grover, Davinder S. "When You Have Cataracts and Glaucoma", Glaucoma Research Foundation, Oct. 29, 2017.

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).

Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).

Tsai, James C. "High Eye Pressure and Glaucoma", Glaucoma Research Foundation, Oct. 29, 2017.

International Search Report in International Application No. PCT/US2020/028962 dated Jun. 2, 2020.

U.S. Appl. No. 16/389,404, filed Apr. 19, 2019, US20200330275A1, Oct. 22, 2020, Combination Treatment Using Phaco and ELT.

U.S. Appl. No. 16/389,437, filed Apr. 19, 2019, US20200330281A1, Oct. 22, 2020, Excimer Laser Fiber Illumination.

U.S. Appl. No. 16/389,359, filed Apr. 19, 2019, US20200330279A1, Oct. 22, 2020, Calibration System for Improving Manufacture Tolerance in Excimer Laser Optical Fibers.

U.S. Appl. No. 16/389,446, filed Apr. 19, 2019, US20200330266A1, Oct. 22, 2020, Combination Treatment Using ELT.

U.S. Appl. No. 16/389,460, filed Apr. 19, 2019, US20200330274A1, Oct. 22, 2020, Methods of Transverse Placement in ELT.

U.S. Appl. No. 16/389,425, filed Apr. 19, 2019, US20200330280A1, Oct. 22, 2020, Personalization of Excimer Laser Fibers.

U.S. Appl. No. 16/389,386, filed Apr. 19, 2019, US20200330157A1, Oct. 22, 2020, Enhances Fiber Probes for ELT.

* cited by examiner

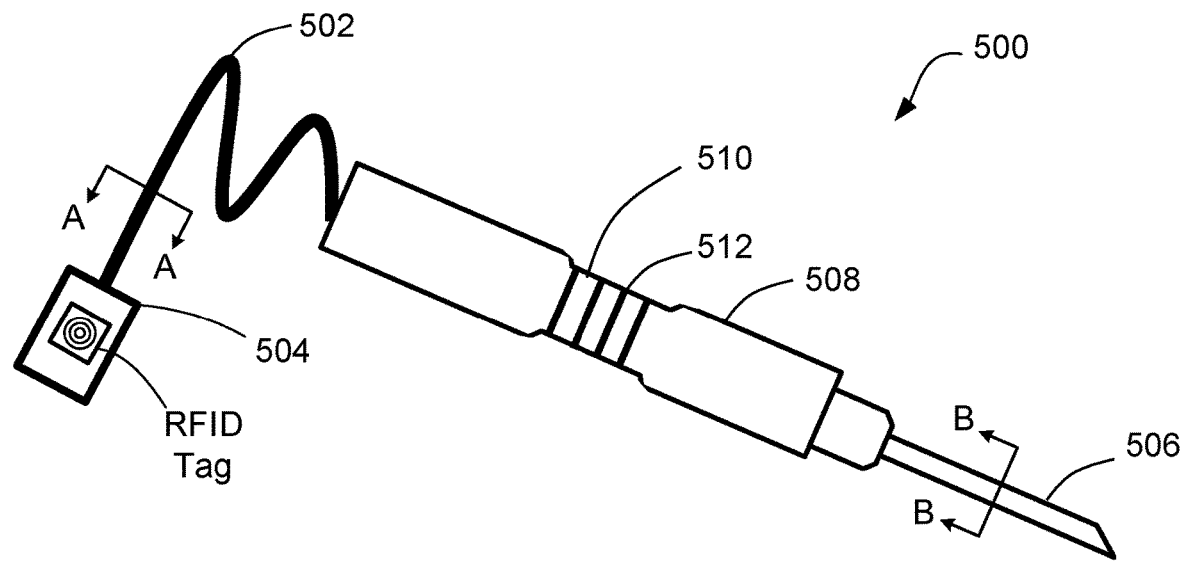
FIG. 4
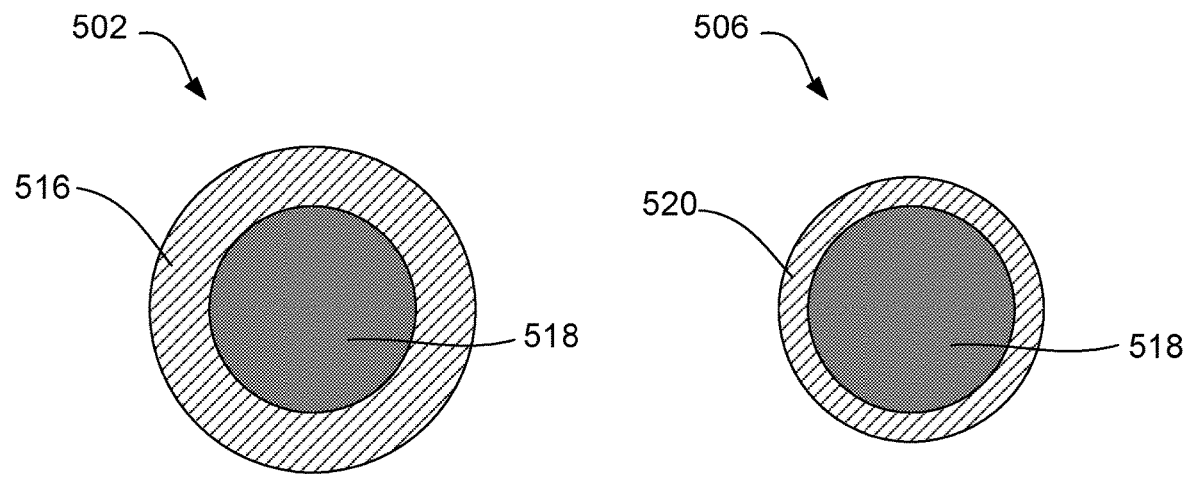
FIG. 5  FIG. 6

AUTHENTICATION SYSTEMS AND METHODS FOR AN EXCIMER LASER SYSTEM

TECHNICAL FIELD

The disclosure relates to medical devices, and, more particularly, to an excimer laser system including a means for authenticating probes to be used with the excimer laser system.

BACKGROUND

In the medical industry, there are many surgical devices, instruments and systems comprised of individual components that must work together properly to ensure treatment is performed safely and as intended. For example, medical laser systems are used to treat various conditions in various practice areas (i.e., urology, neurology, otorhinolaryngology, general anesthetic ophthalmology, dentistry, gastroenterology, cardiology, gynecology, and thoracic and orthopedic procedures). Medical laser systems consist of a laser unit, which generates laser radiation, and a separate laser probe having an optical fiber adapted to direct laser radiation from the laser, through the fiber and to the treatment area.

Specific components of a laser system can be designed by a manufacturer to be utilized with other specific components. For example, there are a variety of medical optical fibers available in the marketplace that can be used with laser systems. Currently available laser systems may provide laser light at various wavelengths and thus may be used for particular purposes and procedures. As such, optical fibers to be used with these laser systems may have varying sizes (diameter, length, etc.), be made of various materials, operate at various temperatures, operate at various wavelengths, and have physical characteristics (e.g., bend radii). Specific components of a laser system can be designed by a manufacturer to be utilized with other specific components. For example, there are many varieties of medical optical fibers available in the marketplace that can be used with laser systems that are used in medical procedures. Furthermore, the manufacturer of one component may also manufacture other components of a laser system, or may certify that these other components can be used with the manufacturer's own components.

Prior to beginning a medical procedure, it is important that the proper optical fiber be connected to the laser unit that is to be used for the medical procedure. Oftentimes, the manufacturer of the laser unit recommends usage of particular brands of optical fibers and/or particular optical fibers with the laser unit. When one of the components being used is not a certified product, the full capabilities of the system may not be achieved and may further cause malfunctions, endangering patient safety. For example use of an improper optical fiber can result in damage to the equipment, delay in conducting a medical procedure until the proper optical fiber is obtained, and/or result in the potential for an ineffective, damaging, or potentially life-threatening medical procedure.

SUMMARY

The present invention provides a system for authenticating laser probes for use with a laser system. In such a system, the elements generally include a laser unit and single-use, disposable laser probes to be coupled to the laser unit, each laser probe having an optical fiber adapted to direct laser radiation from the laser unit, through the fiber, and to the treatment area. The laser unit comprises a control system for operating the laser unit, including controlling output of laser radiation to a laser probe coupled to the laser unit. The laser unit further includes a means for authenticating any given laser probe to determine whether the laser probe is suitable and/or authorized to operate with the laser unit. In particular, the laser unit includes an RFID reader for reading data embedded in an RFID tag associated with the laser probe upon attachment of the laser probe to the laser unit. The data from the RFID tag is analyzed by the control system and a determination is made as to whether the laser probe is authentic (i.e., suitable for use with the laser unit). In the event that the laser probe is determined to be authentic, the control system allows for transmission of laser radiation to the laser probe and thus a procedure can be performed using the laser probe. In the event that the laser probe is determined to not be authentic, the control system prevents transmission of laser radiation to the laser probe.

The authentication analysis is based on a correlation of the RFID tag data with known, predefined authentication data stored in a database, either locally in the laser unit, or stored in a remote database. The known, predefined authentication data is controlled by the owner/manufacturer of the laser unit, such that the owner/manufacturer can determine what laser probes are to be used with the laser unit. The owner/manufacturer may set a specific authentication key or provide for specific identity numbers that are proprietary to the owner/manufacturer. As such, the RFID tag data for any given laser probe must include a corresponding unique identifier (i.e., authentication key or identity number) in order to be deemed authentic. The RFID tag data may include other information and/or characteristics associated with the laser probe and optical fiber. For example, in some embodiments, the RFID tag data further includes operational history information of the laser probe. As such, in some embodiments, it is further possible to utilize the control system to deauthenticate a laser probe based on operational history, such as in the event that the probe has already been used and/or reached the suggested maximum number of laser pulses, thereby preventing further use of the laser probe with the laser unit.

Accordingly, the authentication system of the present invention ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

BRIEF DESCRIPTION OF THE DRAWINGS

FIG. 4 shows an embodiment of a probe for use with the excimer laser system.

FIG. 5 shows a cross-sectional view of the probe taken along line A-A of FIG. 4.

FIG. 6 shows a cross-sectional view of the probe taken along line B-B of FIG. 4.

DETAILED DESCRIPTION

Figure 1:
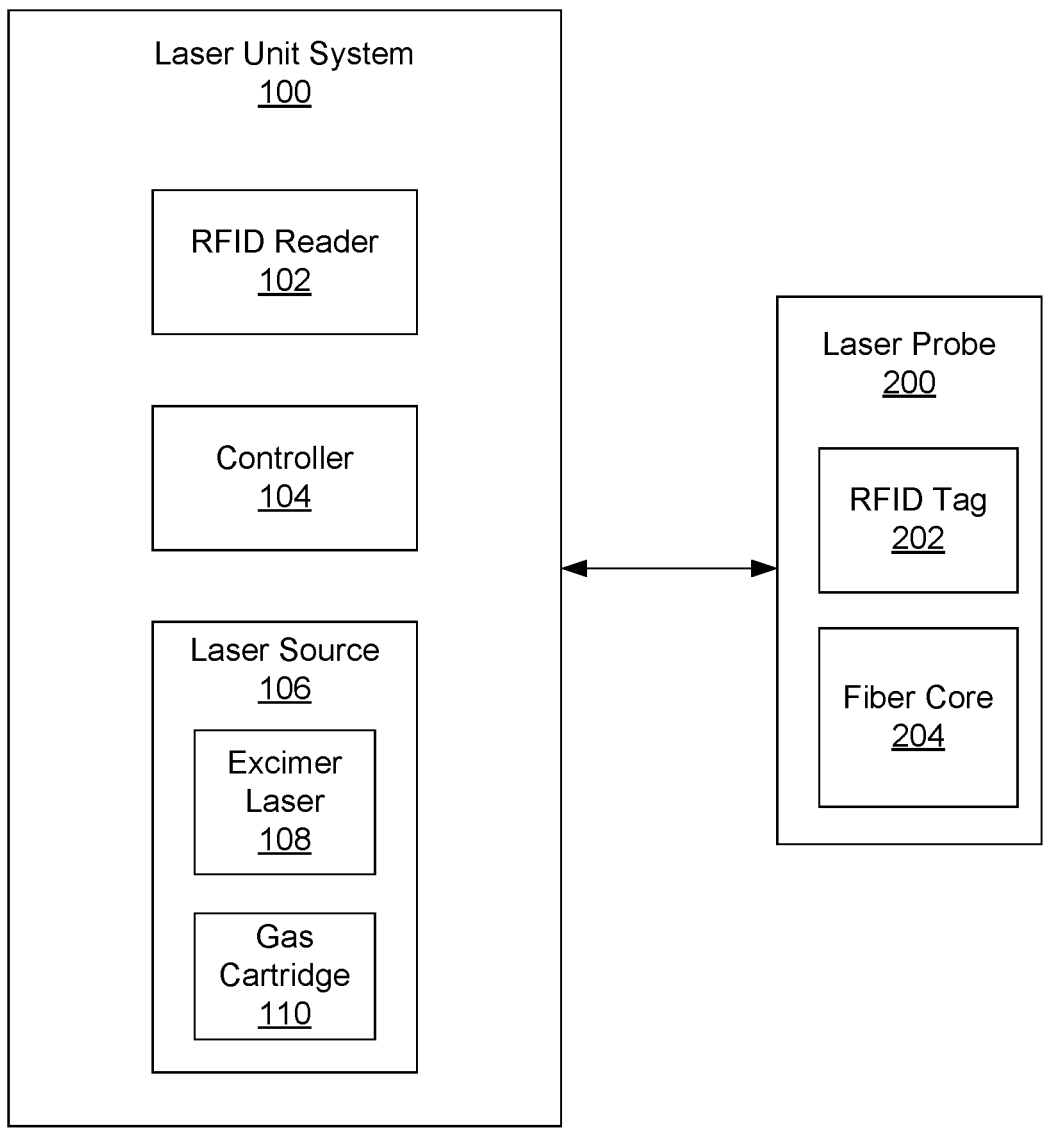
FIG. 1 diagrams an excimer laser system of the present disclosure.

The invention provides a system for authenticating laser probes for use with a laser system. In such a system, the elements generally include a laser unit and single-use, disposable laser probes to be coupled to the laser unit, each laser probe having an optical fiber adapted to direct laser radiation from the laser unit, through the fiber, and to the treatment area. The laser unit comprises a control system for operating the laser unit, including controlling output of laser radiation to a laser probe coupled to the laser unit. The laser unit further includes a means for authenticating any given laser probe to determine whether the laser probe is suitable and/or authorized to operate with the laser unit. In particular, the laser unit includes an RFID reader for reading data embedded in an RFID tag associated with the laser probe upon attachment of the laser probe to the laser unit. The data from the RFID tag is analyzed by the control system and a determination is made as to whether the laser probe is authentic (i.e., suitable for use with the laser unit). In the event that the laser probe is determined to be authentic, the control system allows for transmission of laser radiation to the laser probe and thus a procedure can be performed using the laser probe. In the event that the laser probe is determined to not be authentic, the control system prevents transmission of laser radiation to the laser probe.

Accordingly, the authentication system of the present invention ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

The laser unit and laser probe of the present invention is particularly well suited for intraocular procedures in which laser treatment of target tissues is desired. In particular, the laser probe and laser unit of the present invention is preferably used for treating glaucoma and useful in performing a laser trabeculostomy. However, it should be noted that a laser probe consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

FIG. 1 diagrams an excimer laser system, including a laser unit system 100 and a laser probe 200 to be attached to the laser unit system 100. The system 100 includes an RFID reader 102, a controller 104 (also referred to herein as a "control system 104"), and a laser source 108. The laser probe 200 includes an RFID tag 202 and a fiber core 204. As will be described in greater detail herein, many of the components of the laser unit system 100 may be contained in a housing, such as a moveable platform, to be provided in a setting in which the procedure is to be performed (e.g., operating room, procedure room, outpatient office setting, etc.) and the probe 200 may connect to the housing for use during treatment. Upon coupling the probe 200 to the housing, the fiber core 204 is coupled to the laser source 108 and adapted to direct laser radiation from the laser source 108, through the fiber, and to the treatment area.

The laser source 108 may include an excimer laser 110 and a gas cartridge 112 for providing the appropriate gas combination to the laser 110. The excimer laser 110 is a form of ultraviolet laser that generally operates in the UV spectral region and generates nanosecond pulses. The excimer gain medium (i.e., the medium contained within the gas cartridge 114) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 110 of the present system 100 is an XeCl excimer laser and emits a wavelength of 308 nm.

The controller 104 provides an operator (i.e., surgeon or other medical professional) with control over the output of laser signals (from the laser source 108 to the fiber core 204) and, in turn, control over the transmission of laser energy from the fiber core 204 of the probe 200. However, prior to providing an operator with control over laser output, the laser probe 200 undergoes an authentication procedure to determine whether the laser probe 200 is in fact suitable for use with the laser unit system 100. In particular, upon coupling the laser prober 200 to the system 100, the RFID reader 102 reads data embedded in the RFID tag 202 of the laser probe 200, wherein such RFID tag data is analyzed to determine authenticity of the laser probe 200.

Figure 2:
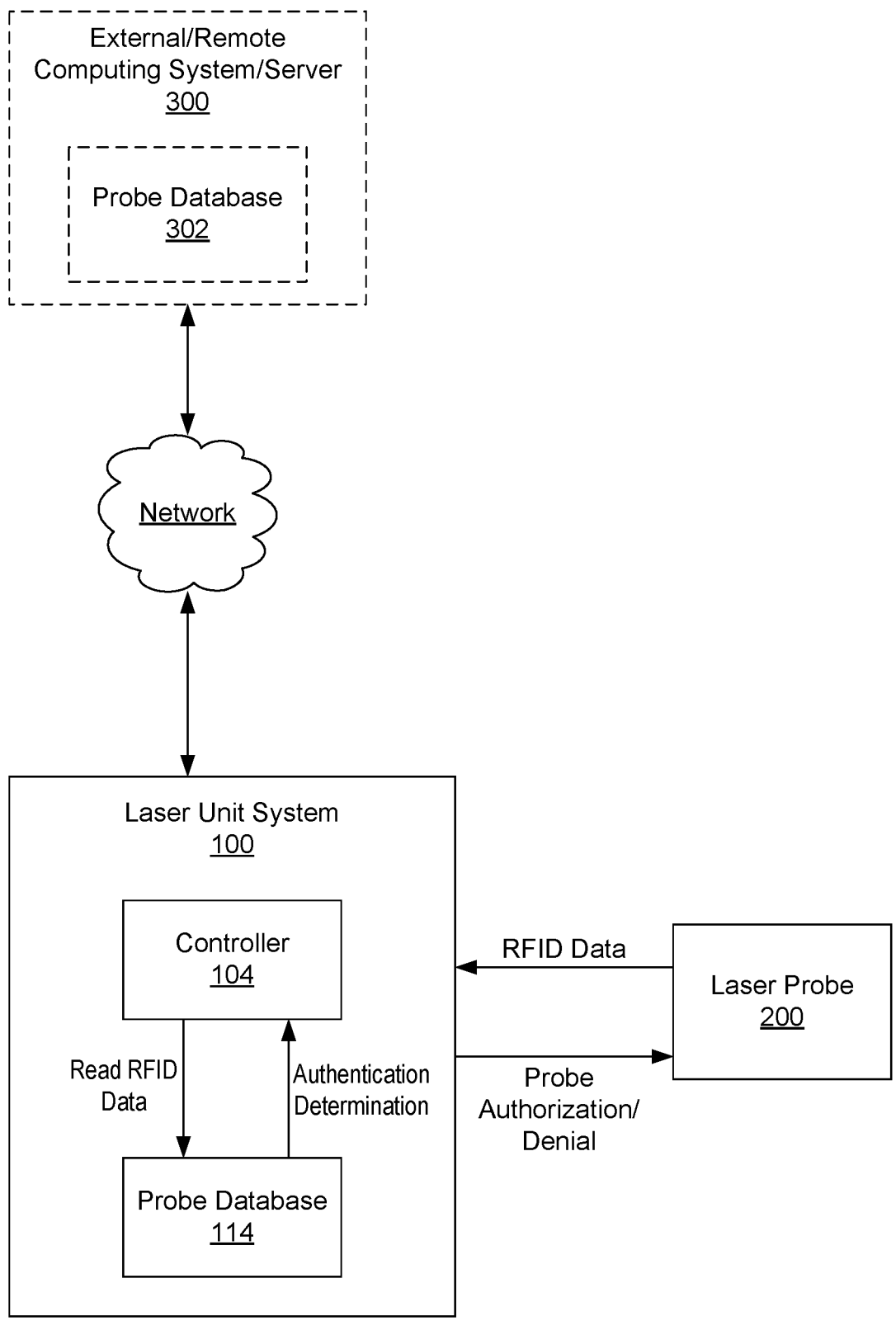
FIG. 2 diagrams the excimer laser system of the present disclosure and authentication of a laser probe to be used with the excimer laser system.

FIG. 2 diagrams the laser system 100 and authentication of a laser probe 200 to be used with the laser system 100. The data from the RFID tag is read by the RFID reader, and then analyzed by the controller 104. A determination is made as to whether the laser probe is authentic (i.e., suitable for use with the laser unit) based on the authentication analysis. In the event that the laser probe is determined to be authentic, the controller 104 allows for transmission of laser radiation to the laser probe 200 and thus a procedure can be performed using the laser probe 200. In the event that the laser probe is determined to not be authentic, the controller 104 prevents transmission of laser radiation to the laser probe 200.

The controller 104 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 104 may include a hardware processor coupled to non-transitory, computer-readable memory containing instructions executable by the processor to cause the controller to carry out various functions of the laser system 100 as described herein, including controller laser and/or illumination output.

The authentication analysis is based on a correlation of the RFID tag data with known, predefined authentication data stored in a database, either a local database (i.e., probe database 114) forming part of the laser unit system 100, or a remote database hosted via a remote server 300 (i.e., probe database 302). For example, in some embodiments, the system 100 may communicate and exchange data with a remote server 300 over a network. The network may represent, for example, a private or non-private local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web).

The known, predefined authentication data stored in the database (database 114 or database 302) may be controlled by the owner/manufacturer of the laser unit 100, for example, such that the owner/manufacturer can determine what laser probes are to be used with the laser unit. For example, the owner/manufacturer may set a specific authentication key or provide for specific identity numbers that are proprietary to the owner/manufacturer. As such, the RFID tag data for any given laser probe must include a corresponding unique identifier (i.e., authentication key or identity number) in order to be deemed authentic.

One approach to uniquely identifying a laser probe is to authenticate the probe by using a private key. In such an approach, both the laser system 100 and the RFID tag 202 are taught an identical key. The RFID tag 202 and laser system 100 then operate in conjunction to authenticate the key. More specifically, the laser system 100 generates a random, unique challenge number. The RFID tag 202 uses this challenge, in combination with the key to generate a response of an authentication code. The method for generating this code (known as a hash function) masks the value of the key. Another approach to uniquely identifying a laser probe is to use unique and unchangeable identity numbers. This approach can be used if there is a region of memory (e.g., a serial or model number), that can only be written by the RFID manufacturer. The protection is realized by ensuring that the manufacturer only provides tags with legal identification numbers, which prevents simple duplication of legitimate tags.

The RFID tag data may include other information and/or characteristics associated with the laser probe and optical fiber. For example, in some embodiments, the RFID tag data further includes operational history information of the laser probe. As such, in some embodiments, it is further possible to utilize the controller 104 to deauthenticate a laser probe based on operational history, such as in the event that the probe has already been used and/or reached the suggested maximum number of laser pulses, thereby preventing further use of the laser probe with the laser unit.

As generally understood, RFID technology uses electromagnetic fields to automatically identify and track tags attached to objects. As previously noted, the RFID tag associated with the laser probe contains electronically-stored information. The RFID tag may either be read-only, having a factory-assigned serial number that is used as a key into a database, or may be read/write, where object-specific data can be written into the tag by the system user. Field programmable tags may be write-once, read-multiple; "blank" tags may be written with an electronic product code by the user. The RFID tag contains at least three parts: an integrated circuit that stores and processes information and that modulates and demodulates radio-frequency (RF) signals; a means of collecting DC power from the incident reader signal; and an antenna for receiving and transmitting the signal. The tag information is stored in a non-volatile memory. The RFID tag includes either fixed or programmable logic for processing the transmission and sensor data, respectively.

The RFID reader transmits an encoded radio signal to interrogate the tag. The RFID tag receives the message and then responds with its identification and other information. This may be only a unique tag serial number, or may be product-related information such as a stock number, lot or batch number, production date, or other specific information. Since tags have individual serial numbers, the RFID system design can discriminate among several tags that might be within the range of the RFID reader and read them simultaneously.

In some embodiments, the RFID tag may be a passive tag, which collects energy from the RFID reader of the laser system interrogating radio waves. In some embodiments, the RFID tag may be an active tag, which includes a local power source (e.g., a battery) and may operate hundreds of meters from the RFID reader of the laser system.

Figure 3:
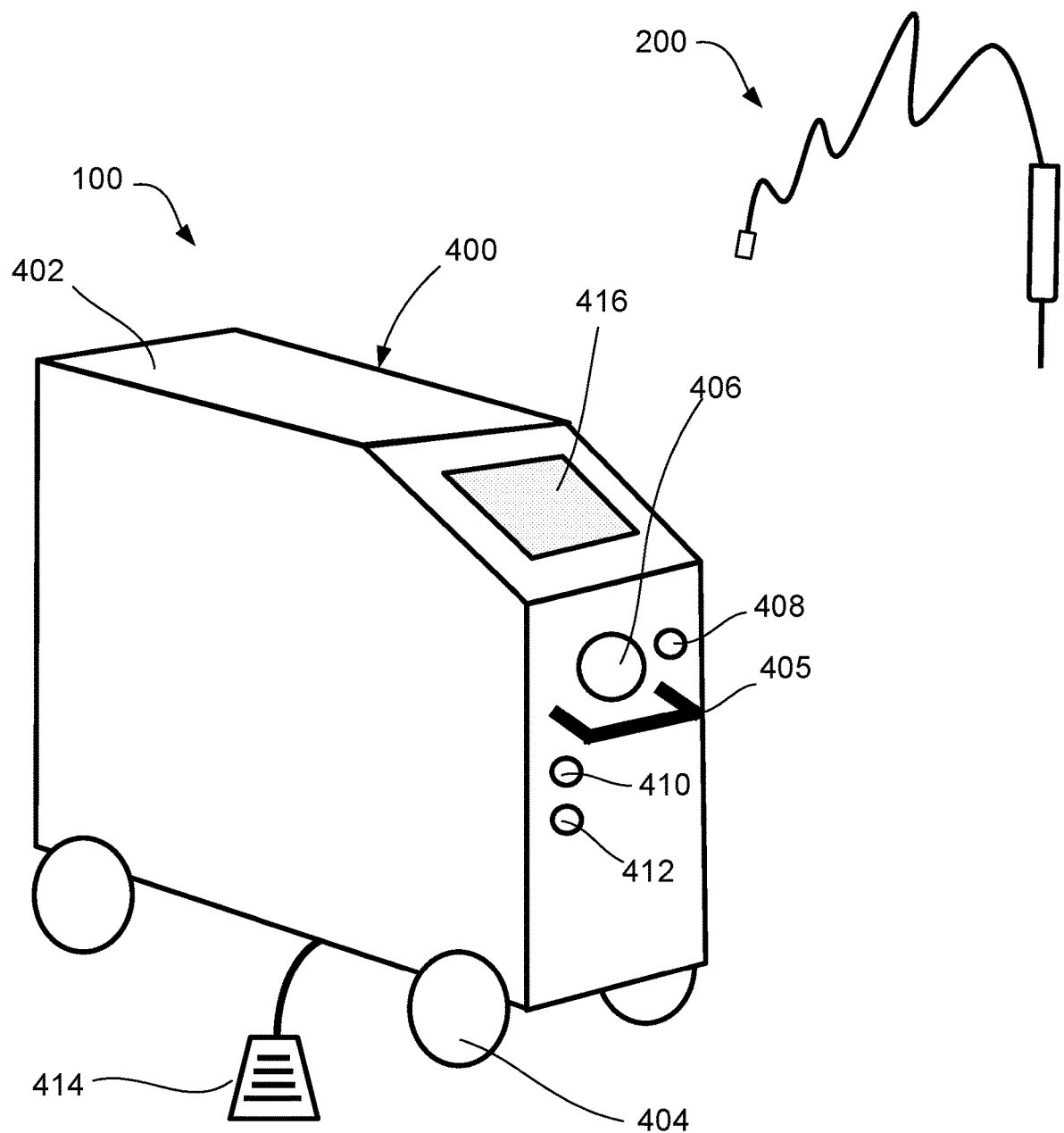
FIG. 3 shows an embodiment an excimer laser unit.

FIG. 3 shows an embodiment an excimer laser unit 100 provided in an instrument 400. As previously described, one or more components of the system 100 can be contained within the instrument 400. In the present embodiment, the RFID reader 102, controller 104, and laser source 108 (including the excimer laser 110 and gas cartridge 112) are contained within a housing 402. The housing 402 has wheels 404 and is portable. The instrument 400 further includes a push-pull handle 405 which assists with portability of the instrument 400. The instrument 400 further includes a connection port 406 for receiving a connecting end of the laser probe 200 to establish a connection between the fiber core 204 and the laser source 108. It should further be noted that the RFID reader 102 may be located in proximity to the connection port 406 to allow reading of data from the RFID tag 202 that is provided on a connecting end of the laser probe 200. The instrument 400 further includes various inputs for the operator, such as fiber probe cap holder 408, an emergency stop button 410, and a power switch 412. The instrument 400 further includes a foot pedal 414 extending from the housing 402 and is operable to provide control over the delivery of shots from the excimer laser 410 to the fiber core 204 of the probe 200. The instrument 400 further includes a display 416, which may be in the form of an interactive user interface. In some examples, the interactive user interface displays patient information, machine settings, and procedure information.

FIG. 4 shows an embodiment of a probe 500 for use with the excimer laser system 100. The probe 500 is a single use, disposable unit. The probe 500 generally includes a fiber core coupled to the laser source 108 by way of a connector 502 (elongated cord) extending from the body of the probe 500 and having a connection assembly 504 configured to be received within the connection port 406 of the instrument 400. The RFID tag 202 is provided on the connection assembly 504, such that, upon coupling the connection assembly 504 to the connection port 406 of the laser unit system 100, data embedded in the RFID tag 202 can be read by the RFID reader 102. The probe 500 further includes a delivery tip 506 from which laser energy (from the fiber core) may be emitted. The probe 500 includes a handheld body 508, which may include a finger grip 510 with ridges or depressions 512. The body 508 of the handheld probe 500 may be metal or plastic.

FIGS. 5 and 6 show cross-sectional views of the probe 500 taken along line A-A and line B-B of FIG. 4, respectively. As shown, a fiber optic core 518 runs through the probe 500 and forms part of the connector 502. A protective sheath 516 surrounds the fiber optic core 518. In some examples, the protective sheath 516 is a protective plastic or rubber sheath. The fiber optic core 518 further form part of the delivery tip 506 of the probe 500. A metal jacket 520 surrounds the fiber optic core 518 and optical fiber 520. In some instances, a stainless steel jacket 520 surrounds and protects the fiber optic core 518.

Figure 7:
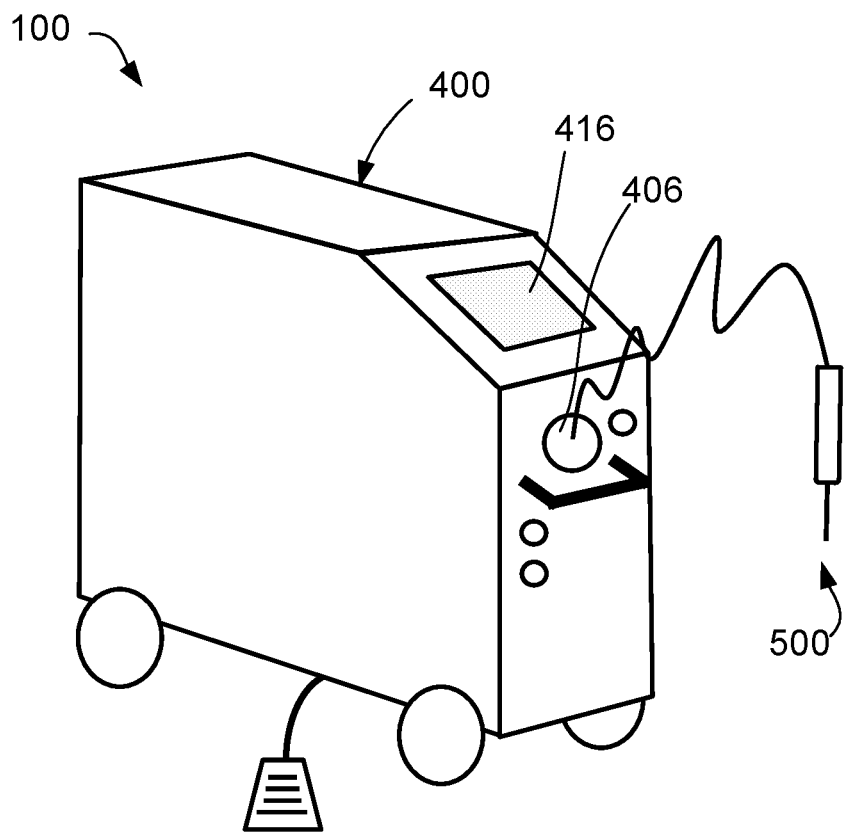
FIG. 7 shows an embodiment a laser probe attached to an excimer laser unit.
Figure 8:
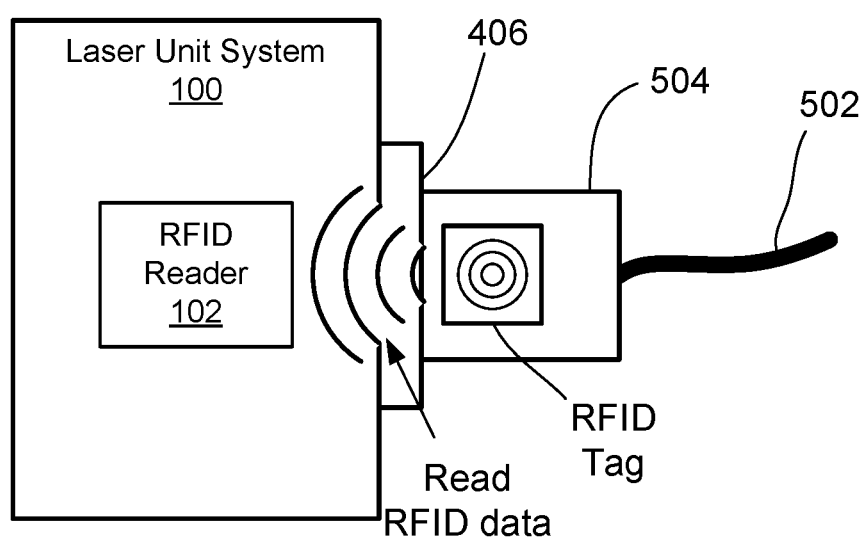
FIG. 8 shows an enlarged view of a connection between the laser probe and the excimer unit and initial RFID reading to determine authenticity of the laser probe.

FIG. 7 shows an embodiment a laser probe 500 attached to a laser unit system 100. As previously described, upon attachment of the laser probe 500 to the system 100 (i.e., coupling between the connection assembly 504 of the probe 500 and connection port 406 of the system 400), the RFID reader 102 reads data embedded in the RFID tag associated with connection assembly 504. FIG. 8 shows an enlarged view of a connection between the laser probe 500 and the system 100 and initial RFID reading to determine authenticity of the laser probe 200. The data from the RFID tag is analyzed by the controller 104 and a determination is made as to whether the laser probe is authentic (i.e., suitable for use with the laser unit). In the event that the laser probe 200 is determined to be authentic, the controller allows for transmission of laser radiation to the laser probe 200. In the event that the laser probe 200 is determined to not be authentic, the controller 104 prevents transmission of laser radiation to the laser probe.

Accordingly, the authentication system of the present invention ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system for use in treating an eye condition, the system comprising:
    a laser unit comprising:
        a radio-frequency identification (RFID) reader;
        an excimer laser source;
        a control system configured to control an output of said excimer laser source based, at least in part, on analysis of tag data read by said RFID reader; and
        a connection port; and
    a plurality of single-use, disposable laser probes, wherein each probe of the plurality of single-use, disposable laser probes comprises a connection assembly configured to connect to the connection port of the laser unit, the connection assembly comprising an RFID tag comprising data associated with a unique authentication identifier and operational history of each probe, wherein each probe is further attachable to the laser unit and either activated for use or denied use with the excimer laser source by the control system based on the analysis of said data read by said RFID reader,
    wherein:
        the connection port of the laser unit is configured to receive the connection assembly of a first probe of the plurality of single-use, disposable laser probes such that the RFID tag is readable by the RFID reader while the connection port of the laser unit and the connection assembly of the first probe are connected; and
        the control system is configured to receive the data comprising the unique authentication identifier from the RFID reader and determine, based at least in part on the unique authentication identifier, that the first probe is compatible for use with the laser unit.

2. The system of claim 1, wherein said RFID tag comprises a passive tag.

3. The system of claim 2, wherein said passive tag provides the data in response to electromagnetic energy emitted from said RFID reader.

4. The system of claim 1, wherein said RFID tag comprises an active tag.

5. The system of claim 4, wherein said active tag continuously broadcasts signals, including said data, to be received by said RFID reader.

6. The system of claim 1, wherein said analysis comprises correlating said data, read by said RFID reader, with at least a set of predefined authentication data stored either locally or remotely and controlled by a manufacturer of the laser unit.

7. The system of claim 6, wherein the first probe is determined to be authentic upon a positive correlation and determined to be inauthentic upon a negative correlation.

8. The system of claim 7, wherein said control system is configured to permit transmission of laser radiation from said excimer laser source to a fiber optic core of the first probe in response to a positive correlation.

9. The system of claim 7, wherein said control system is configured to prevent transmission of laser radiation from said excimer laser source to a fiber optic core of the first probe in response to a negative correlation.

10. The system of claim 6, where said unique authentication identifier comprises an authentication key or identity number.

11. A system for use in treating an eye condition, the system comprising:
    a laser unit comprising:
        a radio-frequency identification (RFID) reader;
        an excimer laser source;
        a controller configured to control an output of said excimer laser source based, at least in part, on analysis of data read by said RFID reader; and
        a connection port; and
    a plurality of single-use, disposable laser probes, wherein each probe of the plurality of single-use, disposable laser probes comprises a connection assembly configured to connect to the connection port of the laser unit, the connection assembly comprising an RFID tag comprising data associated with a unique authentication identifier,
    wherein:
        the connection port of the laser unit is configured to receive the connection assembly of a first probe of the plurality of single-use, disposable laser probes such that the RFID tag is readable by the RFID reader while the connection port of the laser unit and the connection assembly of the first probe are connected; and
        the controller is configured to receive the data comprising the unique authentication identifier from the RFID reader and determine, based at least in part on the unique authentication identifier, that the first probe is compatible for use with the laser unit.

12. The system of claim 11, wherein said unique authentication identifier comprises an authentication key or identity number.

13. The system of claim 11, wherein the controller is further configured to determine, based at least in part on the unique authentication identifier, that the first probe is authorized for use with the laser unit by a manufacturer of the laser unit.

14. A system for use in treating an eye condition, the system comprising:
- a laser unit comprising:
  - a radio-frequency identification (RFID) reader;
  - an excimer laser source;
  - a controller configured to control an output of said excimer laser source based, at least in part, on analysis of data read by said RFID reader; and
  - a connection port; and
- a plurality of single-use, disposable laser probes, wherein each probe of the plurality of single-use, disposable laser probes comprises a connection assembly configured to connect to the connection port of the laser unit, the connection assembly comprising an RFID tag comprising data associated with an operational history of each probe, wherein:

the connection port of the laser unit is configured to receive the connection assembly of a first probe of the of the plurality of single-use, disposable laser probes such that the RFID tag is readable by the RFID reader while the connection port of the laser unit and the connection assembly of the first probe are connected; and the controller is configured to receive the data associated with the operational history of the first probe from the RFID reader and determine, based at least in part on the operational history, that the first probe is permitted for use with the laser unit.

15. The system of claim of 14, wherein the operational history is indicative of whether the first probe has been previously used or if the first probe has been used for a predetermined number of pulses.

* * * * *